United States Patent [19]

Corbett, III et al.

[11] Patent Number: 5,201,903
[45] Date of Patent: Apr. 13, 1993

[54] METHOD OF MAKING A MINIATURE MULTI-CONDUCTOR ELECTRICAL CABLE

[75] Inventors: Scott S. Corbett, III, Portland; W. Eugene Skiens, Wilsonville; John J. Stobie, Portland; Doris A. Beck, Beaverton, all of Oreg.

[73] Assignee: PI (Medical) Corporation, Portland, Oreg.

[21] Appl. No.: 781,494

[22] Filed: Oct. 22, 1991

[51] Int. Cl.$^5$ .......................................... H01R 43/00
[52] U.S. Cl. ........................................ 29/872; 29/855; 128/420.6; 128/421; 128/789; 156/47; 156/48; 156/51; 264/272.14; 439/55
[58] Field of Search ............... 29/855, 856; 128/420.6, 128/421, 784; 264/272.14, DIG. 30, 221; 222; 439/55; 156/47, 48, 51

[56] References Cited

U.S. PATENT DOCUMENTS

| | | | |
|---|---|---|---|
| 3,751,801 | 8/1973 | Praeger et al. | |
| 3,874,077 | 4/1975 | Folk. | |
| 3,881,246 | 5/1975 | Folk. | |
| 4,261,372 | 4/1981 | Hansen et al. | 128/420.6 X |
| 4,495,917 | 1/1985 | Byers | 128/784 X |
| 4,503,124 | 3/1985 | Keane et al. | 428/372 |
| 4,532,930 | 8/1985 | Crosby et al. | 128/421 X |
| 4,537,804 | 8/1985 | Keane et al. | 427/118 |
| 4,614,028 | 9/1986 | Rich | 29/749 |
| 4,640,983 | 2/1987 | Comte | 174/119 |
| 4,809,712 | 3/1989 | Kuzma | 128/420.6 X |
| 4,819,329 | 4/1989 | Haley et al. | 29/860 |
| 4,840,186 | 6/1989 | Lekholm et al. | 128/784 |
| 4,964,414 | 10/1990 | Handa et al. | 128/784 |
| 5,056,531 | 10/1991 | Shimoyama | 128/784 |
| 5,067,903 | 11/1991 | Szyszkowski | 439/55 |
| 5,074,808 | 12/1991 | Beamenderfer et al. | 29/855 X |
| 5,105,811 | 4/1992 | Kuzma | 128/420.6 |
| 5,111,812 | 5/1992 | Swanson et al. | 128/784 X |
| 5,123,422 | 6/1992 | Charvin | 128/420.6 X |

FOREIGN PATENT DOCUMENTS

| | | | |
|---|---|---|---|
| 1115352 | 12/1981 | Canada | 128/784 |
| 2233596 | 1/1991 | Canada | 264/272.14 |

Primary Examiner—Carl J. Arbes
Attorney, Agent, or Firm—Chernoff, Vilhauer, McClung & Stenzel

[57] ABSTRACT

A miniature, electrically-insulated multi-conductor electrical cable suitable for implantation in living bodies and readily connected to sensors or electrodes with terminal pads or to conductors such as printed flex circuit traces of electrical circuits, and a method for preparing such cables. Individual electrical conductors are coated with at least one layer of insulating material. The insulated individual conductors are stranded together, or optionally bound together by an additional layer of insulating material which is compatible with implantation in living bodies. The individual conductors are separated from one another in terminal portions of the cable and are encapsulated in a ribbonizing resin which is trimmed to expose portions of the individual conductors, held by the ribbonization resin at a predetermined pitch to facilitate connection of each of the conductors to a respective conductor trace of a printed circuit or flex circuit.

18 Claims, 6 Drawing Sheets

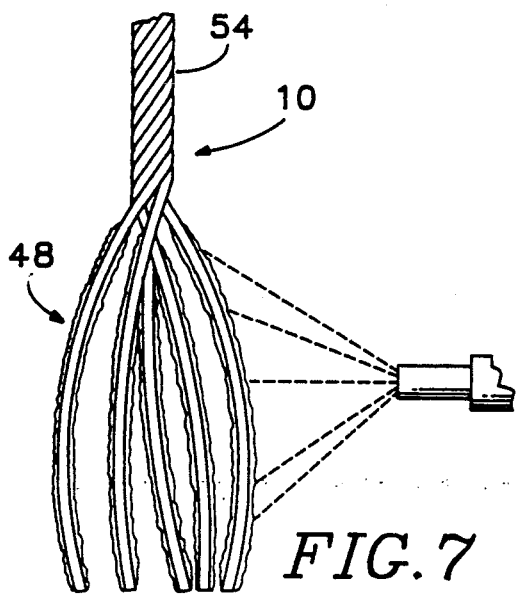
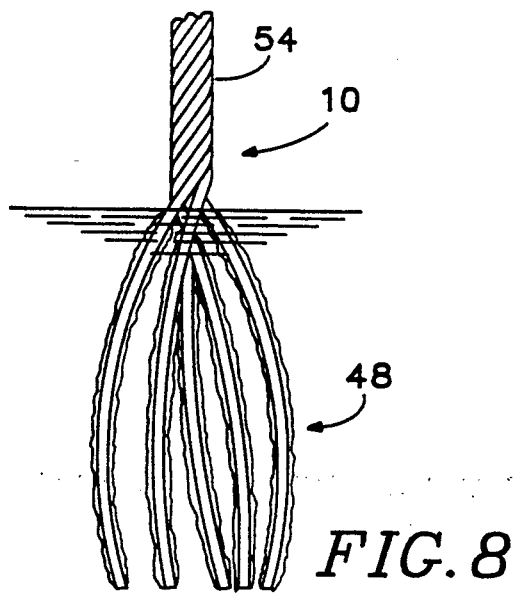
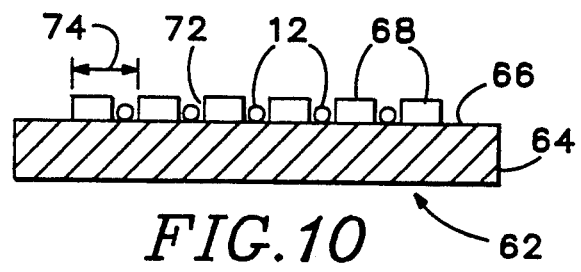
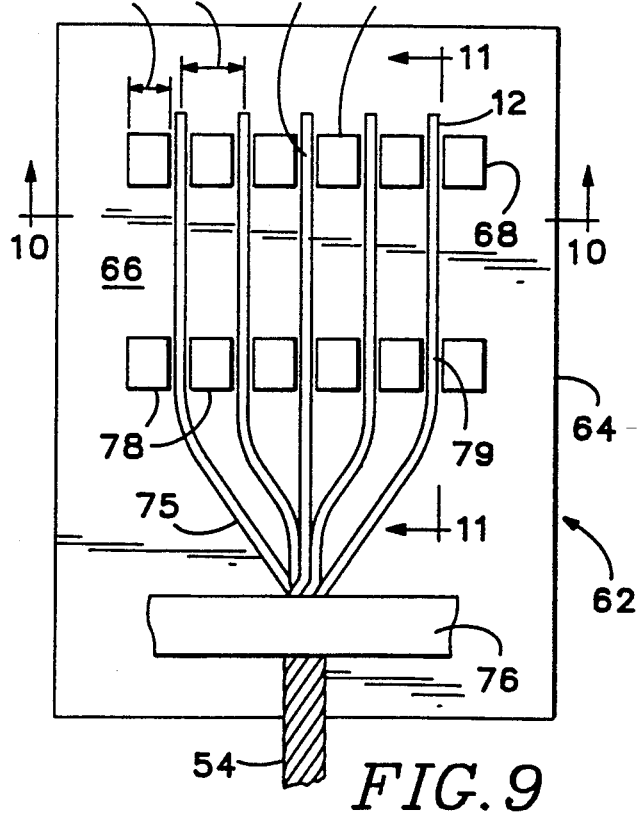
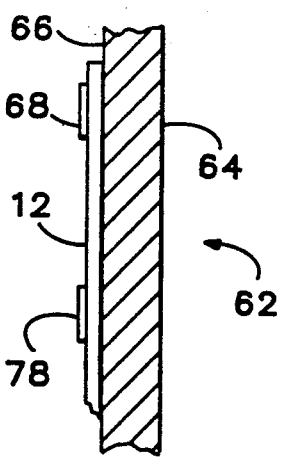

METHOD OF MAKING A MINIATURE MULTI-CONDUCTOR ELECTRICAL CABLE

This invention was made with Government support under Department of Health and Human Services Small Business Innovation Research Contract #N43-NS-0-2391-00, awarded by the National Institute of Neurological Disorders and Stroke, a division of the National Institutes of Health, Department of Health and Human Services. The Government has certain rights in the invention.

BACKGROUND OF THE INVENTION

The present invention relates to miniature electrically insulated multi-conductor electrical cables, particularly those which may be implanted in living persons, and methods for making such cables.

Many miniaturized electrical sensors and control devices may conceivably be implanted in human bodies or may be used in robotic devices. Such sensors and other devices may require reliable transmission of electrical signals, yet may have extremely small current requirements. In many cases flexibility of the conductors is highly desired. For example, electrical signals must be transmitted between an implanted biomedical sensor and an electronically controlled device such as a drug delivery device implanted in a separate location. It may also be desirable to provide electrical stimulation to, or to receive signals from, several separate neurons of the human nervous system, at sites spaced as closely as 100 microns from one another. For example, extremely small biologically compatible cochlear implant devices have been designed which utilize multi-electrode arrays to selectively stimulate portions of the basilar membrane to induce hearing in compromised individuals. It may also be desired to provide functional electrical stimulation by surface electrodes or implanted electrodes to mobilize paraplegics. The smaller and more flexible the cable implanted, the less it is likely to be an irritant to the surrounding tissue.

Ultimately, long term implantation of some biomedical electrical devices may be possible, allowing great advances in diagnostic and remedial medicine. However, a major limiting factor in the usefulness of such devices is the lack of suitable conductors for transmission of electrical energy for device actuation and diagnostic signal transmission. Complications in the desired in-situ application of such electrical conductors are the requirements for flexibility, extremely small size, long-term reliability, and biological compatibility of materials implanted.

It is known to utilize photolithographic techniques to provide flex circuits of fine line noble metal conductors supported by flexible polyimide substrates. A distinct disadvantage of such flexible circuit technology is the limitation of flexibility to a single plane. Additionally, such flex circuits can typically be made only in limited lengths. There is also some concern about the biological compatibility with implantation of such flex circuits because of the materials and chemicals used in the process of their production.

Keane, et al. U.S. Pat. Nos. 4,503,124 and 4,537,804 disclose a conductor insulated with a polyimide overcoated with polyesterimide. The purpose of the Keane coating system, however, is not to provide an implantable cable, and there is no teaching in the Keane et al. patents relating to the formation of terminal portions which can be connected easily to printed circuits.

Haley et al. U.S. Pat. No. 4,819,329 discloses making a cable by holding the terminal portions of individual conductors in a fixture, with the ends of the wires stripped of their normal insulating coating to facilitate connection of the wires to printed circuits or the like. The middle portions of the wires can then be insulated and may be twisted together as a cable.

Handa et al. U.S. Pat. No. 4,964,414 discloses an electrode for implantation. Fine stainless steel wires of less than 25 micron diameter are twisted together and coated with a resin which retains the wires and allows them to be implanted.

Praeger et al. U.S. Pat. No. 3,751,801 discloses a miniature ribbon cable whose insulation is removed from end portions of the conductor wires. Alternate wires are bent in opposite directions to form two rows for soldering to a terminal, at a pitch established by the ribbon cable.

Folk U.S. Pat. Nos. 3,874,077 and 3,881,246 are closely related to each other and disclose the use of grooved templates to receive the several conductors of a cable so that the ends of the conductors may be cut off evenly to receive terminals. However, there is no teaching of how to prepare the conductors to facilitate connection of a very small cable to a printed circuit.

Rich U.S. Pat. No. 4,614,028 discloses a fixture for use in changing the pitch of the conductors of a multi-conductor flat ribbon cable. There is no teaching of how to hold the conductor ends in a desired pitch, however, and the apparatus is not directed to a small cable intended to be implantable.

Lekholm, et al. U.S. Pat. No. 4,840,186 discloses a lead in which multifilament conductors coated with insulation are embedded in a tube wall in a helical arrangement, but the lead so produced is much larger and would be less flexible than desired for certain cable implantations.

Compte U.S. Pat. No. 4,640,983 discloses an electrical conductor intended for implantation into humans, in which multifilament conductors are provided in spiral form and sheathed in a biologically compatible material. The conductor disclosed, however, is much larger than the desired implantable cable with which the present invention is concerned.

What is desired, then, is a multi-conductor electrical cable of extremely small size which can be implanted in a living body without causing continuing irritation, and which is flexible, durable, electrically insulated, and capable of readily being connected electrically to extremely closely spaced terminals.

SUMMARY OF THE INVENTION

The present invention provides a miniature cable and a method for preparing such a cable to answer the aforementioned need for a miniature multi-conductor electrical cable which is implantable in humans, durable, and small and flexible enough not to be an irritant, and which may readily be connected to closely-spaced terminals of electrical circuits.

In accordance with the present invention a miniature multi-conductor electrical cable is provided in which each of a plurality of fine wires of a suitably flexible material such as gold or a platinum-iridium alloy is coated with an insulating material. For example, a thin layer of a resin such as a polyimide covered by a second coating of a polyesterimide insulating material is very effective as an insulating dielectric system, without greatly increasing the force required to bend the cable. Alternatively, a single layer of a polymeric resin such as a polytetrafluoroethylene material (PTFE), perfluorinated ethylenepropylene copolymer (FEP), perfluorinated ethylene-vinyl alkoxy ether copolymer (PFA), silicone, or polyurethane may be used as an insulating coating for individual conductors.

The coated wires of the cable according to the present invention are held together, either by being stranded together, as in a seven-conductor helical stranding, or by an additional coating of an insulating material at least partially surrounding each conductor and interconnecting each conductor with an adjacent conductor along at least an intermediate portion of the length of the conductors. The conductors may be held together by such an additional coating either as a ribbon-like arrangement of parallel conductors, or in a circular configuration as either a solid-core strand or a hollow strand defining a central lumen between the interconnected helically arranged conductors.

According to the invention the individual conductors for such a cable may be prepared, for example, by solution-coating, in the case of the polyimide and polyesterimide insulation materials, or by dispersion coating of an emulsion of a suitable fluorocarbon polymer onto each of the conductors to provide a continuous insulating coating on each conductor.

The ends of a cable according to the present invention may be prepared for connection to terminals of an electrical circuit by the selective removal of one or more of the layers of insulating material, preferably without damaging a primary layer of material insulating each individual conductor, as required to allow the individual conductors to be moved separately to provide a required pitch between them, after which they are formed into a ribbonized terminal portion of the cable. The terminal portions of the separated individual conductor wires are encapsulated in a mechanically supportive insulating material with the conductors at the pitch required for connection of the cable. The encapsulating material is then trimmed, and any remaining insulating material coatings are removed from a selected portion of each conductor to expose the metal surface of the conductor for termination. One preferred manner of such removal of material is the use of a computer-controlled laser.

In a preferred manner of preparing a cable according to the present invention a fixture is provided in which the individual conductors are held parallel with one another at the desired spacing or pitch, while a ribbonizing fixing resin material is cast around the conductors to encapsulate and stabilize them at the correct pitch A preferred ribbonizing, fixing resin is a UV curable silicone resin.

A cable which is one embodiment of the present invention includes an intermediate portion of the cable including several closely adjacent electrical conductors and a ribbonized terminal portion adjacent at least one end of the cable, including a transition portion in which the conductors diverge from one another and merge into a connector portion in which the several conductors are held at a predetermined spacing, or pitch, with respect to each other. In the terminal portion the conductors are preferably encapsulated and thus held in a ribbonized form, but with a respective small length of each of the conductors exposed, free of insulating material, as an electrically connectable portion of the cable.

It is therefore a principal object of the present invention to provide an improved miniature, biologically implantable cable assembly and a system of electrical insulation for the conductors of such a cable assembly.

It is another important object of the present invention to provide a reliable method for assembly and preparation of such a cable.

It is a further object of the present invention to provide a miniature cable which is durable and isotropically flexible.

The foregoing and other objectives, features, and advantages of the, invention will be more readily understood upon consideration of the following detailed description of the invention, taken in conjunction with the accompanying drawings.

BRIEF DESCRIPTION OF THE DRAWINGS

FIG. 7 is a schematic view indicating one manner of removal of insulating material from a terminal portion of a cable according to the present invention in order to prepare the cable for electrical termination.

FIG. 8 is a view schematically indicating another method for removal of layers of insulating material from a terminal portion of a cable according to the present invention in order to provide for electrical termination.

FIG. 9 is a view of a terminal portion of a cable in a fixture for preparing a terminal portion of the cable.

FIG. 10 is a sectional view of the fixture shown in FIG. 9, taken along line 10—10.

FIG. 11 is a sectional view of the fixture shown in FIG. 9, taken along line 11—11.

DETAILED DESCRIPTION OF THE DRAWINGS

Figure 1:
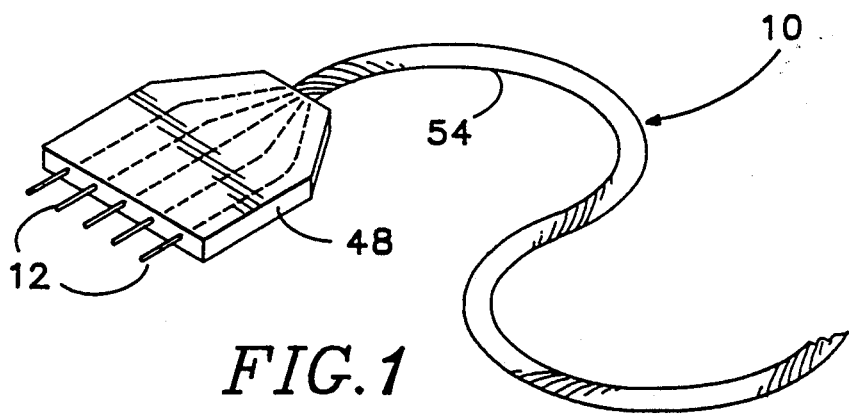
FIG. 1 is a perspective view of an exemplary cable according to the present invention, at a greatly enlarged scale.
Figure 3:
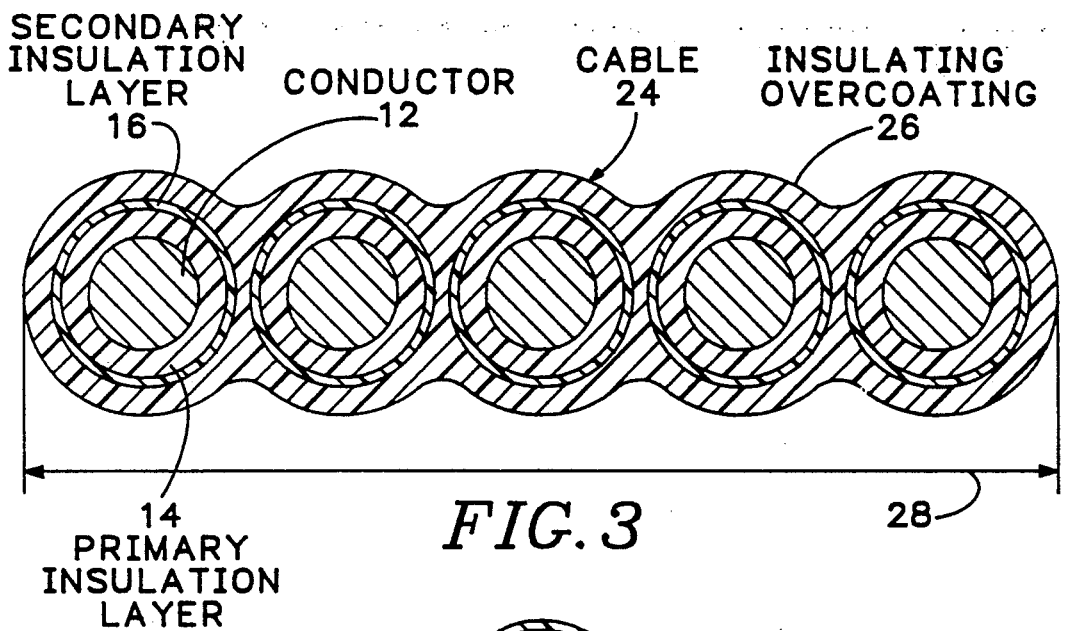
FIG. 3 is a sectional view, at a greatly enlarged scale, showing a ribbon-like flat cable according to the present invention.
Figure 2:
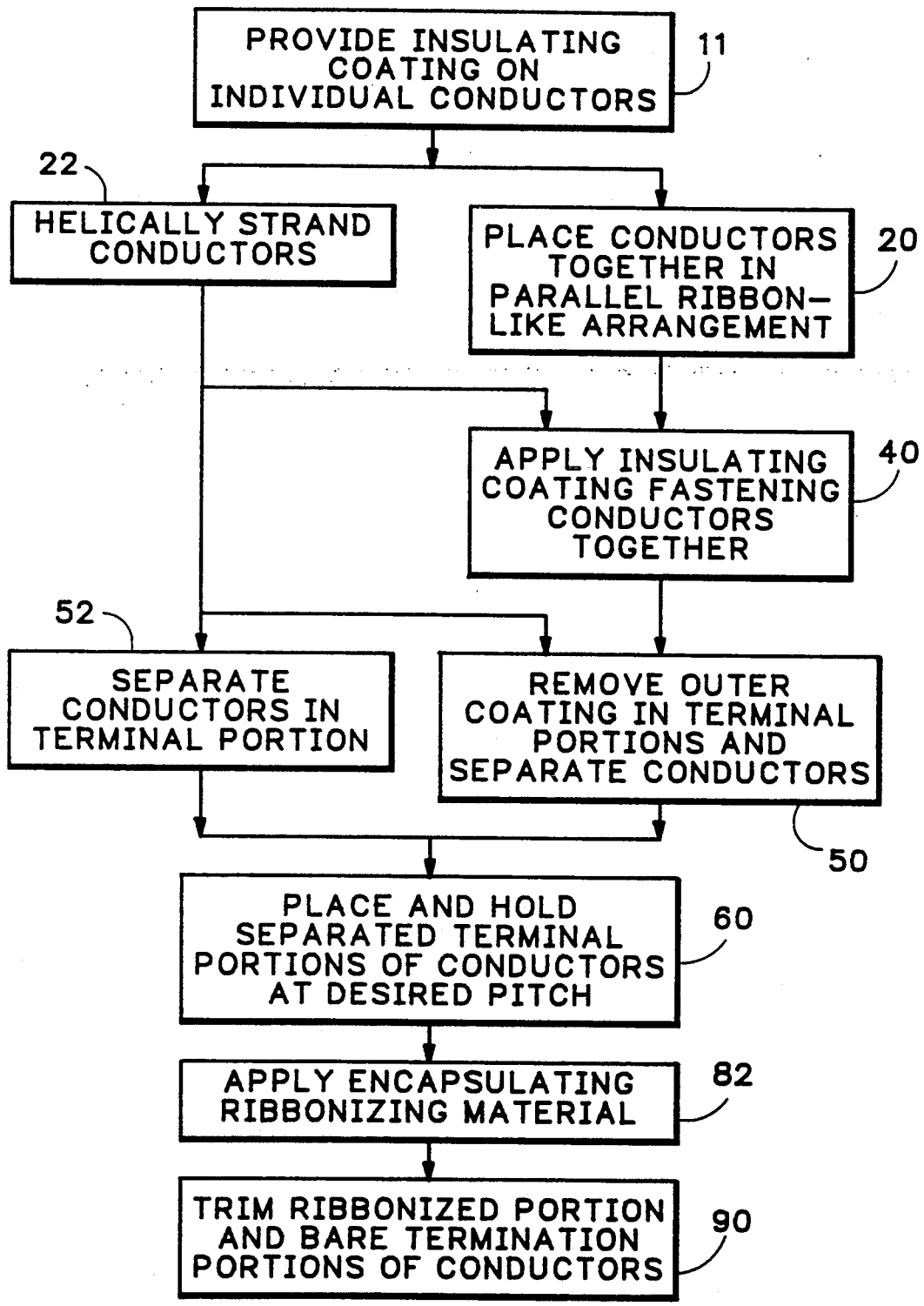
FIG. 2 is a block diagram showing the steps of preparation of an implantable cable according to the present invention.

Referring now to the drawings, a cable 10 according to the present invention, shown in FIG. 1, may be prepared as shown in the simplified flow diagram of FIG. 2. As indicated in block 11 of FIG. 2, individual conductors 12, included in the cable 24 shown in FIG. 3, are preferably of very fine metallic wire prepared by being coated with one or more layers 14, 16 of suitable electrical insulation. Various materials could be used as the conductors 12 and the layers 14, 16 of insulation, depending upon the requirements of a particular application for tensile strength, conductivity, ability to be connected electrically and mechanically, and compatibility with implantation into a living body. A preferred material for a conductor 12, chosen as a compromise of the factors considered, is a wire of platinum-iridium alloy, in which the concentration of iridium is about ten percent or lower, for reasons of biological compatibility. Other possible conductor materials include surgical stainless steel and gold alloys. Gold provides excellent conductivity and flexibility as a conductor 12, but may lack sufficient tensile strength for some applications.

The thickness of the wire of the conductor 12 may vary, depending upon the amount of flexibility and durability required and the electrical load requirements of the application, but, for example, may be equivalent to number 48 through 56 American wire gauge, or in the range of about 30 microns down to about 12 microns, or smaller.

Each individual wire conductor 12 is coated with a primary layer 14 of dielectric insulating material to provide a thin but continuous layer of insulation on each wire. Preferably, the dielectric material to be used as the primary layer 14 should have a high resistance to heat and to chemical solvents which might be employed to remove additional outer layers of dielectric material to be applied over the primary layer 14.

In a preferred embodiment of the invention each individual wire conductor 12 is provided with a primary layer 14 of a polyimide insulation material such as wire enamel available from E. I. DuPont de Nemours & Co. of Wilmington, Del., under the trademark Pyre-M.L. and formulation numbers RC-5019 or RC-5063, for example, having a coating thickness of about 3-7 microns and preferably about 5 microns, over which is applied an additional coating, or secondary layer 16, of a polyesterimide insulation material such as material available from the P. D. George Company of St. Louis, Mo., under the trademark Green Teresod 357, applied to the polyimide primary insulation in a thickness of 1 to 3 microns and preferably about 2 microns. The combination of such insulating materials is superior in its performance as an electrical insulator to a single layer of either material, since the polyesterimide secondary layer 16 is effective to exclude moisture from the relatively hygroscopic polyimide material of the primary layer 14, so that the conductor 12 remains effectively insulated even when implanted. The polyesterimide is also biologically compatible with implantation. Furthermore, it can be selectively removed later without affecting the primary coating layer 14. The layers 14 and 16 of polyimide and polyesterimide insulating materials may be applied using known solution coating techniques. An amorphous perfluorocarbon polymeric material, available from the DuPont Corporation under the trademark TEFLON AF can also be used by solution coating techniques to form the primary layer 14.

Alternatively, the primary insulation layer 14 may be of a polytetrafluoroethylene (PTFE) material such as a PTFE emulsion available from the DuPont Corporation under the trademark TEFLON, or other fluorocarbon polymers, including perfluorinated ethylene-propylene copolymer (FEP) and perfluorinated ethylene-vinyl alkoxy ether copolymer (PFA) applied by known small particle dispersion coating techniques. Satisfactorily applying a secondary insulation layer 16 adherently over a primary layer 14 of polymeric fluorocarbon material is usually difficult, requiring techniques such as etching the surface of the fluorocarbon material to enhance bonding. For that reason, the secondary layer 16 may be omitted when a primary layer 14 is formed of such polymeric fluorocarbon materials as PTFE in an adequate thickness, such as 4 to 6 microns, to reliably insulate the individual conductor 12 electrically. It is also possible to prepare the outer surface of a primary layer 14 of a polymeric fluorocarbon by plasma treatment, after which a secondary layer 16 can be applied.

The primary insulating layer can also be formed of polyurethane, using solution coating application of, preferably, a medical grade aliphatic polyether-based polyurethane such as that available from Thermedics, Inc., of Woburn, Mass., under the trademark TECOFLEX. Other insulating materials including polydimethylsiloxane-based silicones, such as number 996 or number 997 varnish available from Dow Corning of Midland, Mich., may be applied by dip or pad coating methods to form the primary layer 14, or polyurethane-silicone copolymer coating materials such as number X3-6765 or X3-6714 liquid prepolymer, available from Dow Corning, may be applied as by dip coating and then cured by ultraviolet radiation.

Plasma-induced vapor-phase polymerization of methylmethacrylate or vinylidene chloride can also be used to apply a suitably thin, yet uniform and continuous, primary layer 14. Vapor deposition of a paraxylylene polymer such as that available from the Novatran Division of Union Carbide Corporation of Clear Lake, Wis., under the trademark Parylene, is also acceptable for a primary layer 14 of insulating material.

The conductors 12, after each has been coated with an insulating primary layer 14, and, if desired, an insulating secondary layer 16, are placed together with enough other conductors, similarly prepared, to meet the requirements of a particular cable application. For example, they may be placed together in parallel, ribbon-like arrangement, as noted in block 20 of FIG. 2 and illustrated in FIG. 3, or they may be grouped together in a helical stranded arrangement such as any of those shown in FIGS. 4, 5, and 6, as indicated in block 22 of FIG. 2.

As shown in FIG. 3, a cable 24 includes five conductors 12, each having a primary coating 14 and a secondary coating 16 of insulating materials. All are coated further with a third layer, or overcoating 26, of an electrically insulating material which should also be compatible with implantation into a living body. The overcoating 26 may, for example, be of a polyesterimide material similar to that of the secondary layer 16. Use of such material as the overcoating 26 is convenient for its ability to be removed from the individual conductors 12 which have been coated with the primary and secondary layers 14 and 16. The overcoating 26 coats the individual conductors 12, over the primary and secondary layers 14 and 16 of insulating material, and joins the conductors 12 to one another as shown in FIG. 3, to produce a planar, ribbon-like cable 24 having a total width 28 of about 265 microns, or about 0.01 inch.

Figure 4:
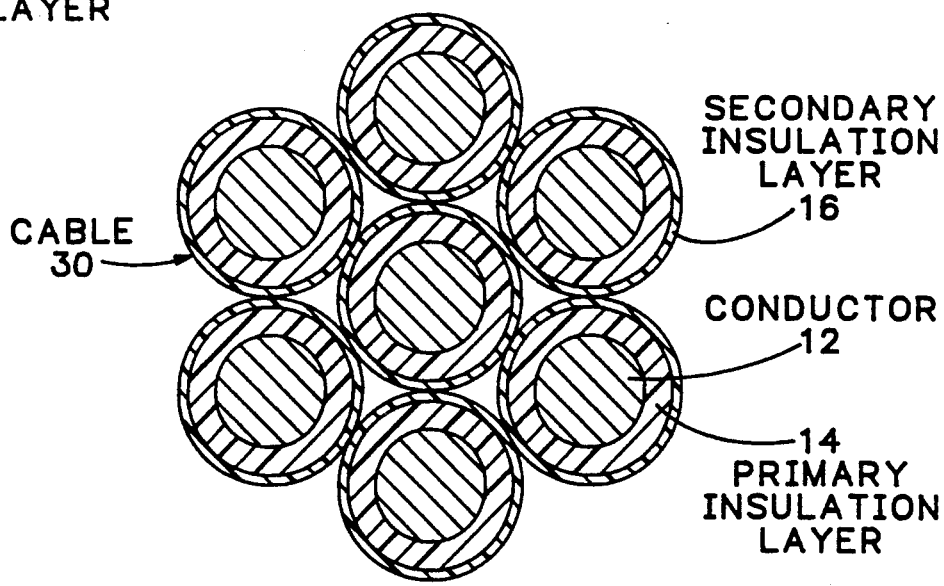
FIG. 4 is a sectional view, at a greatly enlarged scale, of a stranded cable according to the present invention.
Figure 5:
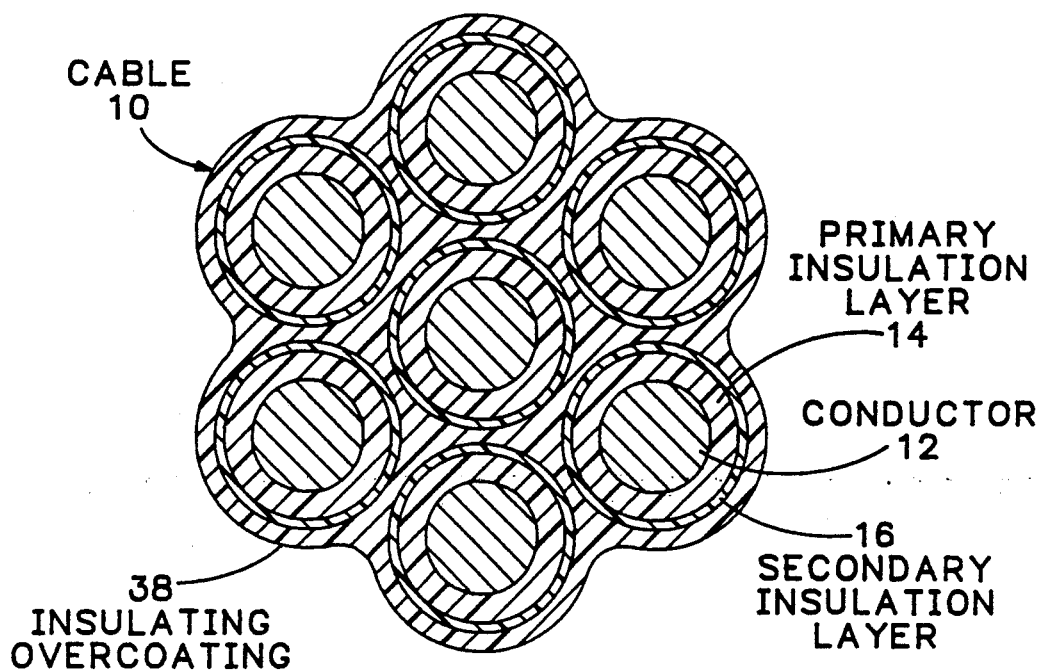
FIG. 5 is a sectional view, at a greatly enlarged scale, of another stranded cable according to the present invention in which the individual conductors are bound together by a coating of insulating material.
Figure 6:
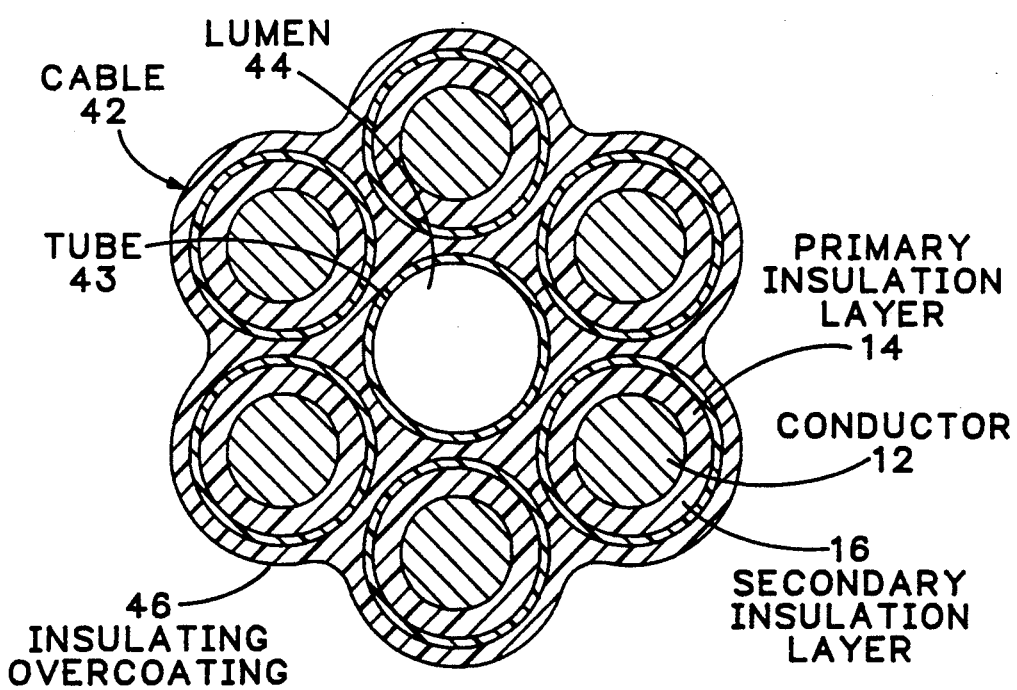
FIG. 6 is a sectional view, at a greatly enlarged scale, of a stranded, cable according to the present invention in which a lumen is defined within the strand.

Groups of individual conductors 12 may also be arranged as a round cable, preferably twisted tightly enough to keep all of the conductors together. For example, a 0.070-inch lay pitch for a cable diameter of 0.001 inch, has been found satisfactory to maintain a helical arrangement configured, for example, as shown in FIGS. 4, 5, and 6. In FIG. 4 a cable 30 includes seven individual conductors 12, each coated by a primary layer of insulating material 14 and a secondary layer 16. This stranding can be performed using a planetary or non-planetary cabler. The entire group of conductors 12 is held together as the cable 30 merely by the effect of the helical twist. Such an arrangement allows the individual conductors 12 to flex and, to some extent, to move longitudinally with respect to one another to promote flexibility of the entire cable 30, allowing the cable 30 to bend in response to a minimum of bending force consistent with having the individual conductors 12 insulated electrically.

As shown in FIG. 5, a generally circular cable 10, a grouping of seven conductors 12 with their coatings 14 and 16 of primary and secondary insulating materials, may be provided further with a third or outer layer, or overcoating 38, of an insulating material, as shown by step 40 in FIG. 2. A polyesterimide material similar to the preferred material of the secondary layer 16 of insulation surrounding each separate conductor 12, such as the previously-mentioned Green Teresod 357 material available from the P. D. George Company, has been found to be satisfactory as such an overcoating 38. To provide biocompatible cable coating systems according to the present invention, the overcoatings 26 or 38 may also be of other materials which can be removed without damage to the particular primary layer 14 of insulating material. For example, polyurethane dissolved in a suitable solvent system such as tetrahydrofuran or dimethylacetamide or similar solvent mixtures may be used to overcoat a stranded or ribbonized cable whose conductors 12 are coated with a primary layer 14 of the polyimide, silicone, PTFE, PFA, FEP, or amorphous perfluorocarbon polymer (TEFLON AF) materials previously mentioned as suitable for the primary layer 14. The previously mentioned TECOFLEX brand medical grade aliphatic polyurethane would be one such satisfactory polyurethane material.

Alternatively, some polymeric fluorocarbons, such as the previously-mentioned amorphous perfluorocarbon available from E. I. DuPont under the trademark TEFLON AF, may be dissolved in certain perfluoronated solvents such as that available from 3-M Company of Minneapolis, Minn. under the trade name Fluorinert FC-75. This solution may then be applied to deposit the overcoat layer 38 or 26 for a stranded or ribbonized cable whose conductors 12 have a primary layer 14 of the silicone, polyurethane, polyimide, PTFE, FEP, or PFA materials mentioned previously as being useful as a primary layer 14.

As yet a further alternative, silicone polymer dispersions or solutions are also suitable to use as the overcoating layer 26 or 38 for a stranded or ribbonized cable according to the invention, where the individual conductors 12 have a primary layer 14 of one of the polyimide, PTFE, FEP, PFA, or amorphous perfluorocarbon (TEFLON AF) insulating materials mentioned previously as being satisfactory for use as such a primary layer 14. Medical grade silicones such as Dow Corning MDX4-4210 or Silastic Q7-2245, both available from the Dow Corning Corp. of Midland, Mich., may suitably be dispersed or dissolved in certain suitable solvents such as xylene, toluene, or VM & P naphtha and used to overcoat such a stranded or ribbonized cable.

As shown in FIG. 6, in a cable 42 six individual conductors 12, each individually coated with a primary insulating material 14 and a secondary coating 16 of insulating materials, are formed into a generally circular cable 42 including an extremely small tube 43 defining a lumen 44 surrounded by individual conductors 12 held together by an overcoating 46 of a dielectric insulating material such as the previously described polyesterimide, polyurethane, or silicone materials. The tube 43 can, for example, be a tube formed of a polyimide material and available from Hudson International, Specialty Products Division, of Trenton, Ga., in sizes as small as an outside diameter of 0.0041 inch and a lumen diameter of 0.0031 inch. The cable 42 can thus function as an extremely small catheter. The conductors 12 of the cable 42 are preferably helically twisted together as a strand to help maintain the round configuration of the cable 42 including the centrally located tube 43.

Not only must the individual conductors 12 be adequately insulated by insulating layer 14 (and secondary layer 16, if appropriate) and an overcoating 26, 38, or 46, as appropriate, but the ends of the cables 10, 24, 30 and 42 must be prepared to be connected to electrical circuits of sensors and control devices as appropriate. The individual conductors 12 can be coated with the coating 14 of primary insulation, and a secondary coating of insulation 16, if desired, and may thereafter be prepared as cables with a required number of individual conductors 12 either twisted together or arranged in a planar, ribbon-like configuration or twisted cable configuration and adhered to one another by an overcoating layer as described previously to produce cable material in long lengths. Thereafter, the cable may be cut to desired lengths for particular applications and the terminal portion at each end of a chosen length of cable material can be prepared to provide for electrical connection to a printed circuit or set of terminal pads by providing the required pitch between adjacent ones of the conductors 12 at the terminal portion of the cable.

In order to minimize the amount of space required for interconnection of the cables according to the present invention to items which must be implanted within a living body, the ends of a cable according to the invention are prepared to include terminal portions 48. The several individual conductors 12 are held in a cable terminal configuration in which parts of the individual conductors 12 are exposed for electrical connection and are held evenly spaced apart from one another with a pitch corresponding to the pitch between exposed terminal pads or conductors of an electrical circuit to which the cable is to be connected.

In each cable in which the individual conductors 12 have been fastened together in their intermediate portion 54 by an overcoating (as in the cable 24 shown in FIG. 3, the cable 30 shown in FIG. 4, the cable 10 shown in FIG. 5, and the cable 42 shown in FIG. 6), the overcoating of insulating dielectric material must be removed from a terminal portion 48 of the cable, as indicated by step 50 of FIG. 2, and the terminal portions of the individual conductors 12 must be separated from one another, as indicated in steps 50 and 52 shown in FIG. 2. It is also acceptable to remove the secondary layer 16 of insulating material from the portions of the individual conductors 12 to be included in the terminal portion of the cable if such a layer is present, but the primary layer 14 of insulating material is preferably kept intact.

As illustrated symbolically in FIGS. 7 and 8, the overcoating or third layer 26, 38 or 46 of insulating material can be removed from the terminal portion 48 of a cable such as the stranded cable 10, for example, by providing a stream of heated air, hot enough to melt or even char such an overcoating layer 38. The secondary layer 16 of insulating material may similarly be removed from each of the individual conductors 12 at the same time, but need not be so removed. The primary insulation layer 14 is left undamaged because of its higher melting and decomposition temperatures.

As represented schematically in FIG. 8, the polyesterimide overcoat 38 and the secondary layer 16 of insulating material of the individual conductors 12 may be removed from the terminal portion 48 of the cable 10 by the use of a solvent which acts on the polyesterimide insulating material without damaging the primary insulating coating 14 of polyimide. Three solvents which have been determined to be superior in selectively attacking an overcoat layer 26, 38, or 46 and secondary layer 16 of polyesterimide are N-methylpyrrolidinone, 1,1,2,2-tetrachloroethane, and cresylic acid. The solvent should be heated to 100°–150° C. (depending on solvent volatility). The terminal portion of the cable 10 is then placed in the hot solvent for a sufficient time, usually less than three minutes, for the solvent to soften and swell the polyesterimide material. The softened material can then be removed easily from the terminal portions of the conductors 12 by brushing it away with a tool such as the back of a scalpel, taking care not to damage the individual conductors 12 in the process. This leaves the individual conductors 12 in the terminal portion 48 of the cable 10 free to be manipulated separately to prepare the cable 10 for termination.

In the case of round cables such as the cable 10, it may be necessary to "ring out" the conductors 12 electrically to be sure that the conductors 12 are arranged correctly and correspondingly at both of the opposite ends of the cable to mate properly with both of a pair of electrical circuit which the cable is intended to interconnect. Next, as indicated in step 60 in FIG. 2, the separated terminal portions of the conductors 12 at an end of the cable are placed in a terminal preparation, or ribbonization, fixture 62 shown in FIGS. 9, 10, and 11, and as indicated in step 60 in FIG. 2.

The ribbonization fixture 62 includes a base 64 having a flat horizontal upper surface 66 upon which are located several spacer pads 68, which may be of generally rectangular shape and which are, for example, formed integrally with the base 64. The spacer pads 68 are preferably aligned with one another in a row aligned transversely with respect to the conductors 12. Each spacer pad 68 preferably has the appropriate width 70 to leave gaps 72 between adjacent spacer pads 68, providing the desired separation distance, or pitch 74, between consecutive ones of the conductors 12 of a cable, such as the cable 10, to facilitate electrical connection of the cable to a printed circuit. Once the individual conductors 12 have been detached from one another by removing an overcoating 38 or the equivalent, as described above, the terminal portion 48 of the cable is placed atop the base 64 of the ribbonization fixture 62. The individual conductors 12 are manipulated, making them diverge from each other in a transition portion 75, as by using tweezers, to place each of the individual conductors 12 into a respective one of the gaps 72, with the conductors lying substantially flat along the upper surface 66 of the base 64. A row of rear spacer pads 78, similar to the spacer pads 68, are separated from each other and located aligned with respective ones of the spacer pads 68 adjacent the transition portion 75 to hold the conductors 12 similarly in gaps 79, maintaining parallelism between the conductors 12. All of the spacer pads 68 and 78 preferably have the same height 80, as is best seen in FIGS. 10 and 11. Preferably, the still-overcoated portion of the cable 10, 24, 30, or 42 which remains helically twisted or in flat planar ribbon form, is held down on the base 64 of the ribbonization fixture, as by use of a small strip 76 of an adhesive tape overlying the cable and adhering to the surface 66 on each side of the cable.

Once the individual conductors 12 have been placed properly in position in a terminal configuration in respective gaps 72 and 79 between the spacer pads 68 and 78 of the ribbonization fixture 62, a quantity of a resin material is cured surrounding transition portion 75 and the terminal portions of the conductors 12 to ribbonize the terminal portion 48 of the cable 10, as indicated as step 82 in FIG. 2. Preferably, a cover sheet 84 of a material which is transparent to ultraviolet light is placed over a small quantity of uncured resin material 86, with the cover sheet 84 supported by the spacer pads 68 and the rear spacer pads 78 so that the flat cover sheet 84 shapes the resin material 86 to provide a flat upper surface while the resin is cured by application of high intensity ultraviolet light. The cover sheet 84 may, for example, be a glass microscope slide cover.

Figure 14:
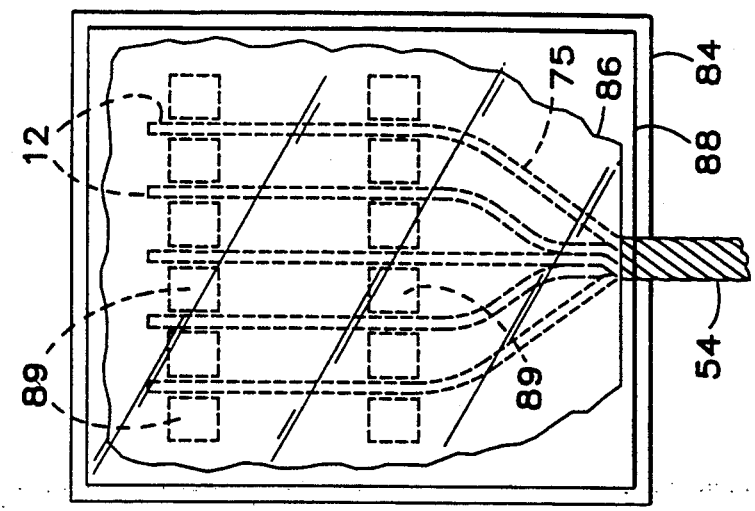
FIGS. 12, 13, 14, 15 and 16 show a terminal portion of a cable according to the present invention at consecutive steps in the process of its preparation.
Figure 13:
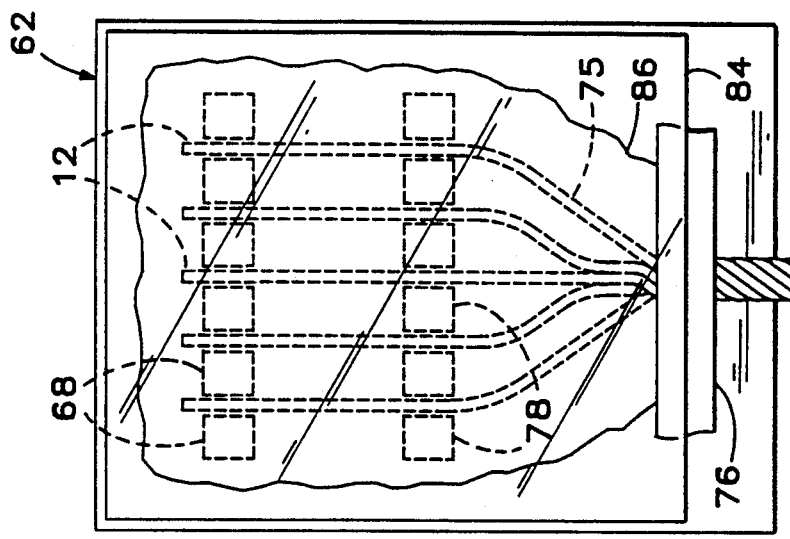
Figure 12:
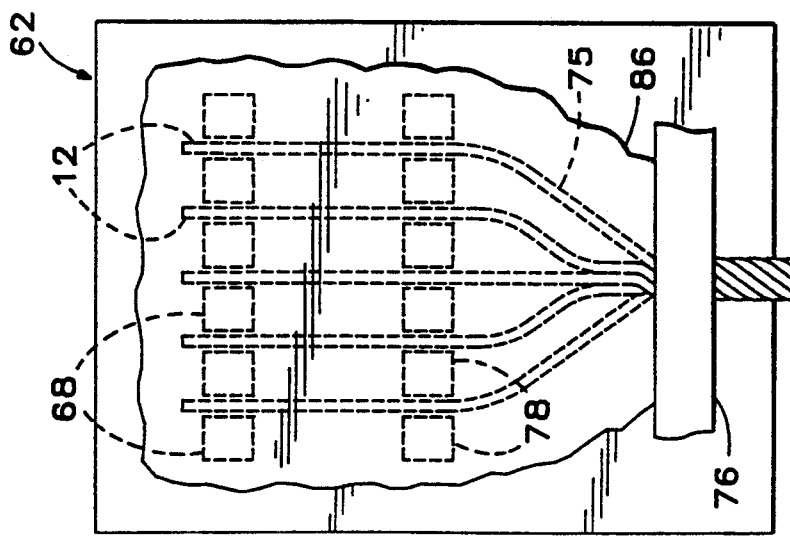

Once the UV-curable resin 86 has been cured the cable end assembly is removed from the ribbonization fixture 62 and may be turned over to expose what had been the underside, which had been resting on the surface 66 of the ribbonization fixture 62. As shown in FIG. 14, an additional controlled amount of resin 86 may then be applied and covered by a second slide cover sheet 88, also transparent to ultraviolet light, to form a second flat surface defined by the second cover sheet 88, with the additional resin material filling and covering the indentations 89 previously made by the spacer elements 68 and 78 which had been used to hold the individual coated conductors 12 properly aligned parallel with each other at the desired pitch 74. The second quantity of resin material 86 is then also cured, as by exposure to high intensity ultraviolet light.

A suitable resin material 86 for forming such a ribbonized cable terminal portion 48 has been found to be a medical grade UV-curable silicone available, for example, from Dymax Corp. of Torrington, Conn., as its Dymax TM UV-curable silicone No. 20234, which can be cured by brief exposure to high intensity ultraviolet light.

Figure 15:
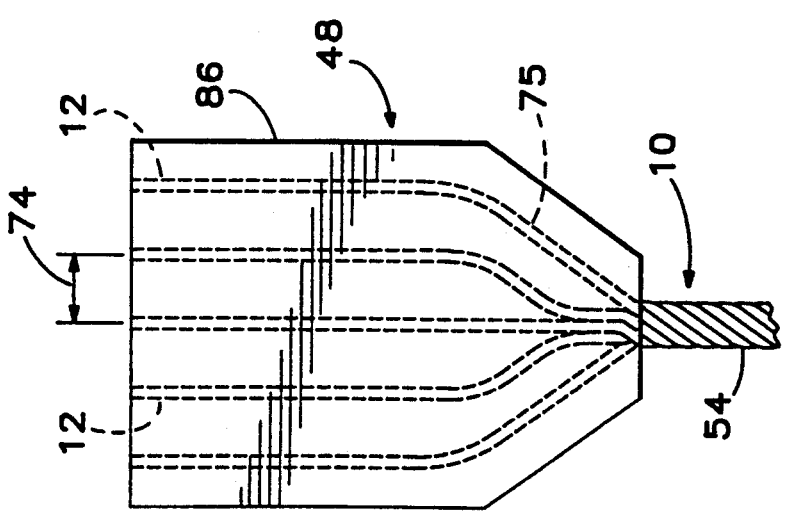

Once the resin material has been cured on both sides (or immediately after removing the cable and assembly from the ribbonization fixture 62 if it is not desired to use a second quantity of ribbonization resin 86) of the terminal portion 448 of the cable the cover sheets 84 and 88 (as applicable) are carefully removed and the ultraviolet-cured resin is trimmed, as indicated as step 90 in FIG. 2, to leave the terminal portion 48 of the cable preferably in the form such as that shown in FIGS. 1 and 15 of the drawings. Because of the very small size of the terminal portions 48 of the cables according to the invention, having a pitch 74 of, for example, 150 microns between adjacent conductors 12, trimming of the ultraviolet-cured resin material 86 is best accomplished initially by use of a precision cutting die to provide a shape such as that shown in FIG. 15. Thereafter, portions of the individual conductors 12 are bared to permit electrical connection, preferably in an accurately machine-controlled manner such as by the use of a computer-controlled laser beam scanned across the ribbonized terminal portion of the cable, sweeping in a direction perpendicular to the length of the portions of the individual conductors 12 which had been held in the gaps 72 of the fixture 62.

Preferably, multiple sweeps of the laser beam, using a low power laser such as a 25 watt $CO_2$ laser available from Synrad, Inc., of Bothell, Wash., are used to remove the excess cured ribbonizing encapsulation resin material and the primary layer 14 of insulating material without damaging the conductors. As an alternative to use of the $CO_2$ laser, it is also possible to remove the excess portions of ribbonizing resin material 86 and the primary layer 14 of insulation material by use of an excimer laser with a low-power output.

Figure 17:
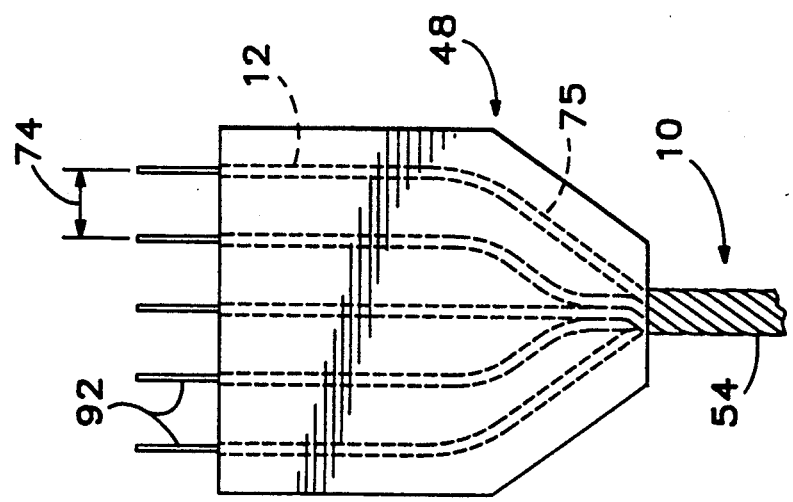
FIG. 17 shows an alternative configuration of the terminal portion of the cable.
Figure 16:
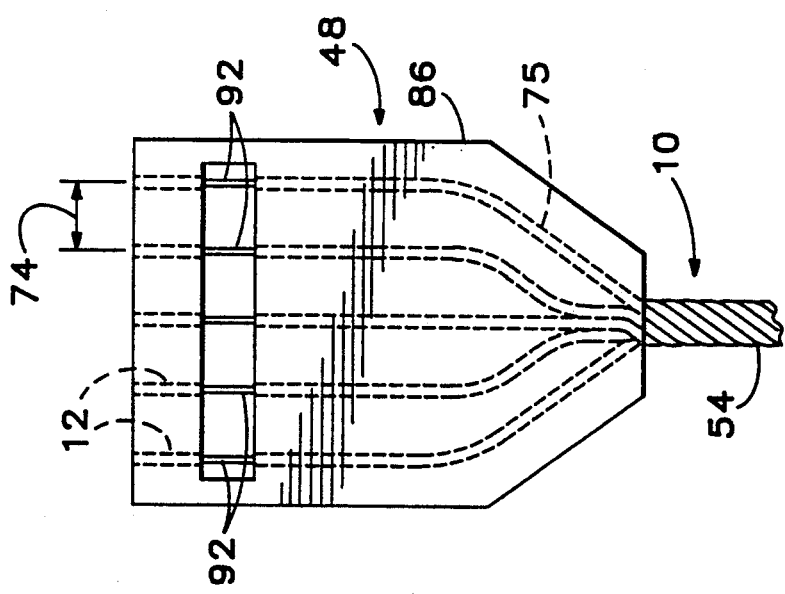

As shown in FIG. 16, the laser may be used to remove ribbonization resin material 86 and any remaining material of secondary and primary layers 16, 14, baring portions 92 of the individual conductors 12 while leaving the conductors 12 supported on each-end of each portion 92 by a quantity of the ribbonization resin 86. Alternatively, the ribbonization material and the secondary and primary insulation layers may be removed at the distal end of the ribbonized terminal portion of the cable as shown in FIG. 17.

Because insulating material such as polyimide used as the primary layer 14 on each of the conductors 12 is somewhat resistant to removal by laser radiation, it may be necessary to remove residue of such a layer 14 by ultrasonic cleaning with a detergent and distilled water, in order to leave a clean and bare metal surface on each of the individual conductors 12.

Electrical connection of the individual conductors 12 may be accomplished by placing the prepared terminal portion 48 of the cable properly in registration with terminal pads or printed circuit conductor traces on a printed circuit to which the cable is intended to be connected and effecting connection by conventional techniques such as suitable wire-bonding techniques.

The steps of preparing and ultimately connecting the terminal portion 48 of the cable are similar when the primary layer 14 is of another insulating material such as a layer of Teflon (PTFE), silicone, or polyurethane material, the critical steps being removal of overcoating material causing the insulated individual conductors 12 to adhere to each other, establishing the required pitch between terminal portions of the conductors 12, applying, curing, and trimming a ribbonizing material 86 to maintain the positions of the conductors 12, and then baring the portions of the conductors 12 to be connected electrically.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method of making a miniature multiconductor electrical cable, comprising:
   (a) coating a plurality of fine elongate electrical conductors with a first continuous layer of a first insulating material;
   (b) arranging respective intermediate portions of all of said plurality of fine elongate electrical conductors closely adjacent one another;
   (c) placing and holding a respective terminal portion of each of said fine elongate electrical conductors in a fixture in a terminal configuration with said terminal portions of said conductors substantially parallel with one another and spaced apart from one another in a planar arrangement at a predetermined pitch;
   (d) ribbonizing said terminal portions of said fine elongate electrical conductors by applying and curing a layer of insulating ribbonizing material over said terminal portions, embedding said terminal portions in said material and thereby holding said terminal portions in a terminal configuration.

2. The method of claim 1, including coating each of said plurality of fine elongate electrical conductors with a second layer of a second insulating material covering said first layer of insulating material.

3. The method of claim 2, including the further step of placing said plurality of fine elongate electrical conductors in a desired arrangement closely alongside one another after coating said conductors with said first and second layers, and coating said plurality of conductors with a third layer of a third insulating material of a thickness effective to interconnect said plurality of conductors with one another along a predetermined portion of the lengths of said plurality of conductors.

4. The method of claim 3 wherein said third insulating material is a polyesterimide material.

5. The method of claim 3 wherein said third insulating material is a polyurethane material.

6. The method of claim 3 wherein said third insulating material is a silicone material.

7. The method of claim 3 wherein said third insulating material is a polymeric fluorocarbon material.

8. The method of claim 3, including the steps of forming said predetermined portions of said fine elongate electrical conductors in a generally circular solid strand configuration over a predetermined intermediate portion of said cable, and holding said predetermined portions of said conductors in said solid strand configuration by said third layer.

9. The method of claim 3, including the step of applying said third layer so as to interconnect said predetermined portions of adjacent ones of said plurality of fine elongate electrical conductors to define a central lumen between said plurality of conductors.

10. The method of claim 3, including applying said third layer of insulating material to hold said plurality of fine elongate electrical conductors parallel with each other in a generally planar flexible ribbon-like configuration.

11. The method of claim 1 wherein said first insulating material is a polyimide resin.

12. The method of claim 1 wherein said first insulating material is a polyurethane material.

13. The method of claim 1 wherein said first insulating material is a silicone material.

14. The method of claim 1 wherein said first insulating material is a fluorocarbon polymer.

15. The method of claim 1 wherein said first layer has a radial thickness in the range of 3 microns to 6 microns.

16. The method of claim 1 wherein said second layer is of a polyesterimide resin material and has a radial thickness less than that of said first layer.

17. The method of claim 1, including the step of stripping away said layers of insulating material from each of said fine elongate electrical conductors in a portion of said ribbonized portion of said cable so as to lay bare a predetermined portion of each of said conductors while holding said conductors arranged with said predetermined pitch therebetween adjacent said terminal portion of each of said conductors.

18. The method of claim 17, including the step of stripping away said insulating material from each of said fine elongate electrical conductors by use of a laser beam scanned in an appropriate pattern under computer control to provide a terminal portion of said cable with a predetermined configuration.

* * * * *